United States Patent [19]
Foster et al.

[11] Patent Number: 5,955,648
[45] Date of Patent: Sep. 21, 1999

[54] HYBRID WILD RICE PRODUCTION UTILIZING CYTOPLASMIC-GENETIC MALE STERILITY SYSTEM

[75] Inventors: Ken Foster; ZanHua Zhu, both of Davis, Calif.

[73] Assignee: NorCal Wild Rice, Woodland, Calif.

[21] Appl. No.: 08/797,918

[22] Filed: Feb. 12, 1997

Related U.S. Application Data

[62] Division of application No. 08/430,915, Apr. 28, 1995, Pat. No. 5,773,680.

[51] Int. Cl.⁶ .............................. A01H 1/04; A01H 5/00
[52] U.S. Cl. .................... 800/274; 800/320; 800/260; 800/298
[58] Field of Search ................... 800/200, 205, 800/230, DIG. 52, DIG. 55, 274, 320, 298, 260; 47/58, DIG.
[58] Field of Search ............................................ 1

[56] References Cited

PUBLICATIONS

Forsberg et al. Sources, Maintenance, and Utilization of Parental Material. In: Hybridization of Crop Plants. American Society of Crop Science, WI. pp. 65–81, 1980.

Emerging Food R&D Report. Food Technology Intelligence, Inc. Information Access Company, IAC Newsletter Database, 1994.

Oelke et al. Wild Rice—new interest in an old crop. Cereal Foods World. vol. 42, pp. 234–247, 1997.

*Primary Examiner*—Douglas W. Robinson
*Assistant Examiner*—Melissa L. Kimball
*Attorney, Agent, or Firm*—Rothwell, Figg, Ernst & Kurz

[57] ABSTRACT

The present invention relates to a wild rice seed, a wild rice plant, and a method for producing a wild rice hybrid seed. More specifically, the invention relates to a hybrid wild rice seed and plant produced using a cytoplasmic-genetic male sterility system. The $F_1$ hybrid seed is produced by crossing male sterile wild rice plants with restorer wild rice plants.

11 Claims, 4 Drawing Sheets

HYBRID WILD RICE PRODUCTION UTILIZING CYTOPLASMIC-GENETIC MALE STERILITY SYSTEM

This is a divisional of application Ser. No. 08/430,915, filed Apr. 28, 1995 now U.S. Pat. No. 5,773,680.

BACKGROUND OF THE INVENTION

The present invention relates to a wild rice seed, a wild rice plant, a wild rice variety and a method for producing a wild rice hybrid seed.

Wild rice, Zizania palustris L. (Dore), is an important cultivated specialty crop in Minnesota and California. Despite having "rice" as part of its name, wild rice Zizania palustris L. (Dore) is very different and distinct from domestic or white rice (Oryza sativa L.). The name "wild rice" arises from its aquatic growth habit. Wild rice, the only cultivated species in Zizania, has a chromosome number of 2n equal to 30, while cultivated rice has 2n equal to 24 chromosomes.

Consumption of processed wild rice has grown steadily at 10% to 15% per year since wild rice cultivation began in mid-1960's. As well as direct retail sales, wild rice is used as a supplemental ingredient by numerous large food companies. Total crop value in 1991 at farm level was approximately $20 million.

Wild rice is a paddy-grown crop, adapted to cooler temperatures and deeper water than domestic rice (Oryza sativa L.). This allows wild rice production in Minnesota and parts of California, where rice or other cereals are not adapted. Wild rice in California is grown without the use of pesticides or herbicides. The crop possesses sufficient vigor that competition and good water management are sufficient to suppress weeds. This is important because of the difficulty in obtaining chemical registrations for specialty crops and because it contributes to an overall reduction in pesticide use. Wild rice is widely used to add variety and contrast in flavor, texture, and color to grain-based dishes (rice, pasta, etc). The wild rice grain is nutritious, is relatively easy to prepare for eating, and has excellent storage properties.

In the mid-1980's, competition between newly developed California production and Minnesota resulted in a dramatic decline in wild rice prices. New products containing wild rice as an ingredient increased rapidly during this period. Production efficiencies have since allowed both regions to adjust to the new market conditions. Incremental growth in wild rice production will occur as a result of promotional activity and incremental productivity gains. However, a higher level of productivity is needed to reduce the cost of wild rice production and to promote new uses of wild rice.

Wild rice has numerous unusual seed properties (Kovach, D. and Bradford, K., Temperature Dependence of Viability and Dormancy of Zizania palustris var interior seeds stored at high moisture contents, Annals of Botany, 1992; Kovach, D. and Bradford, K., Imbibitional damage and desiccation tolerance of wild rice Zizania palustris seeds, Journal Experimental Botany, 1992). Wild rice seeds have the following properties: a) a short life in commercial storage (1–2 years); b) die if they are allowed to dry out below about 25%, and c) have a deep, intractable dormancy at harvest. These factors combine to hinder development of a wild rice seed industry, and these characteristics have been the focus of much of the public research on wild rice. Also, the cropping patterns in Minnesota and parts of California rely on volunteer reseeding for establishing crop stands. Because of this, these areas have difficulty adopting new varieties.

Past progress in breeding wild rice has been achieved through population improvement, both in California by Nor-Cal, Inc. and in Minnesota by the University of Minnesota (Everett, L. A. and Stucker, R. E., A Comparison of Selection Methods for Reduced Shattering in Wild Rice, Crop Science 23:956–960, 1983). The high degree of variability encountered suggests that some continued progress can be made through these methods (Foster, K. W. and Rutger, J. N., Genetic Variation of Four Traits in a Population of Zinzania aquatica, Canadian Journal of Plant Science 60:1–4, 1980). Currently the commercial production of hybrid wild rice is not feasible for a number of reasons. However, the development of a hybrid wild rice would greatly accelerate the usage of this crop and could increase both yield and quality characteristics.

Producing hybrids based on a Cytoplasmic-Genetic Male Sterility (CGMS) system has been used in several crops other than wild rice. For example, sorghum seed is produced by CGMS. The use of hybrids in several cereal crops has failed due to the lack of one or more important characteristics. For example, commercial oats and rye are not hybrids. Extensive efforts to develop hybrid wheat and barley have largely been abandoned due to a low level of heterosis and difficulty of developing good restorer lines. Hybrid rice is important in certain parts of parts of the world including China but has not gained a significant foothold in the U.S., despite considerable public and private research efforts. Lack of success in these crops is attributable to one or more of the following: a) insufficient heterosis, b) poor fertility restoration in the hybrid, c) complicated genetics of fertility restoration, and d) difficulty in obtaining the pollen distribution necessary for seed production.

SUMMARY OF THE INVENTION

The present invention relates to a hybrid wild rice plant, a hybrid wild rice seed, a wild rice variety, and a method for producing hybrid wild rice.

More specifically, the invention relates to a method of producing hybrid wild rice using a Cytoplasmic-Genetic Male Sterility System. The present invention further relates to a method of producing $F_1$ hybrid wild rice seed comprising crossing an A line male sterile wild rice plant with an R line wild rice plant. The present invention also relates to a method of producing hybrid wild rice seed wherein said wild rice seed comprises less than 1.0% self-pollinated seed. The present invention relates to a method of maintaining a male sterile wild rice A line by crossing said A line with a B line wild rice.

The present invention further relates to a wild rice variety having a percentage of male sterile plants of greater than 75%. The present invention further relates to a method of producing seed by growing sterile single cross wild rice plants interspaced in a field with male fertile pollinator plants. The present invention also relates to a hybrid wild rice plant having a yield heterosis value of greater than 30% above either parental line.

DETAILED DESCRIPTION OF THE INVENTION

In order to provide an understanding of several of the terms used in the specification and claims, the following definitions are provided:

Hybrid—The term hybrid is intended to refer to first generation progeny from crossing two non-identical parental lines. Parental lines may be related, as in production of a modified single cross, or unrelated.

Figure 2:
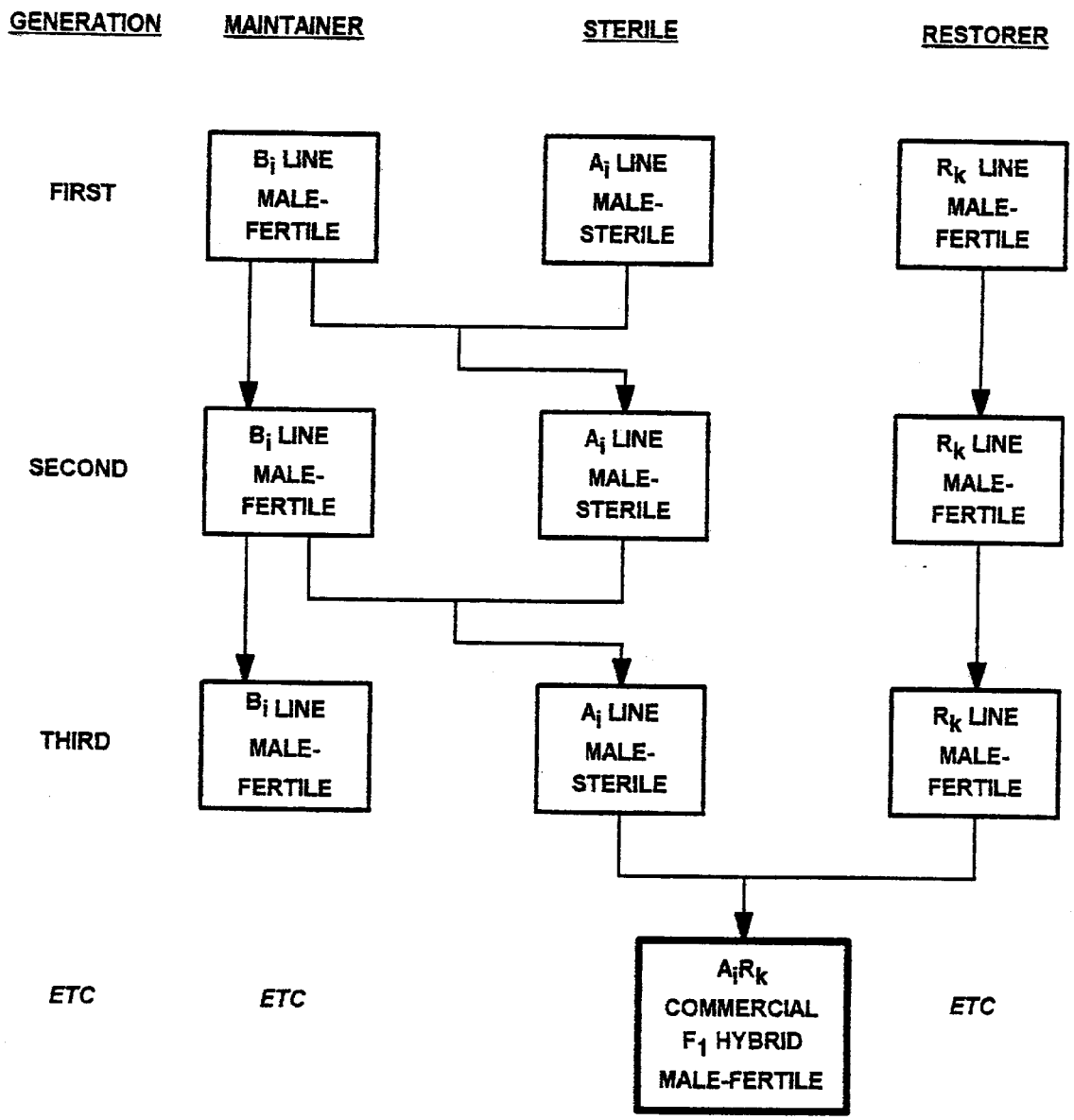
FIG. 2 illustrates a flow diagram showing the production of a single cross $F_1$ hybrid using the Cytoplasmic-Genetic Male Sterility System.

Single cross hybrid—A single cross hybrid is designated $A_iR_K$ and represents the first generation progeny from crossing $A_i$ by $R_K$ ($A_i/R_.$) as shown in FIG. 2 and is the most uniform hybrid type.

Sterile single cross—The term sterile single cross is designated as $A_iB_j$ where $A_i$ is a different line from $B_j$. This cross is 100% male sterile and becomes the seed parent for a subsequent cross, as in a modified single cross, three-way cross, or double cross. The sterile single cross is normally produced to improve seed producing capability of the seed parent.

Figure 3:
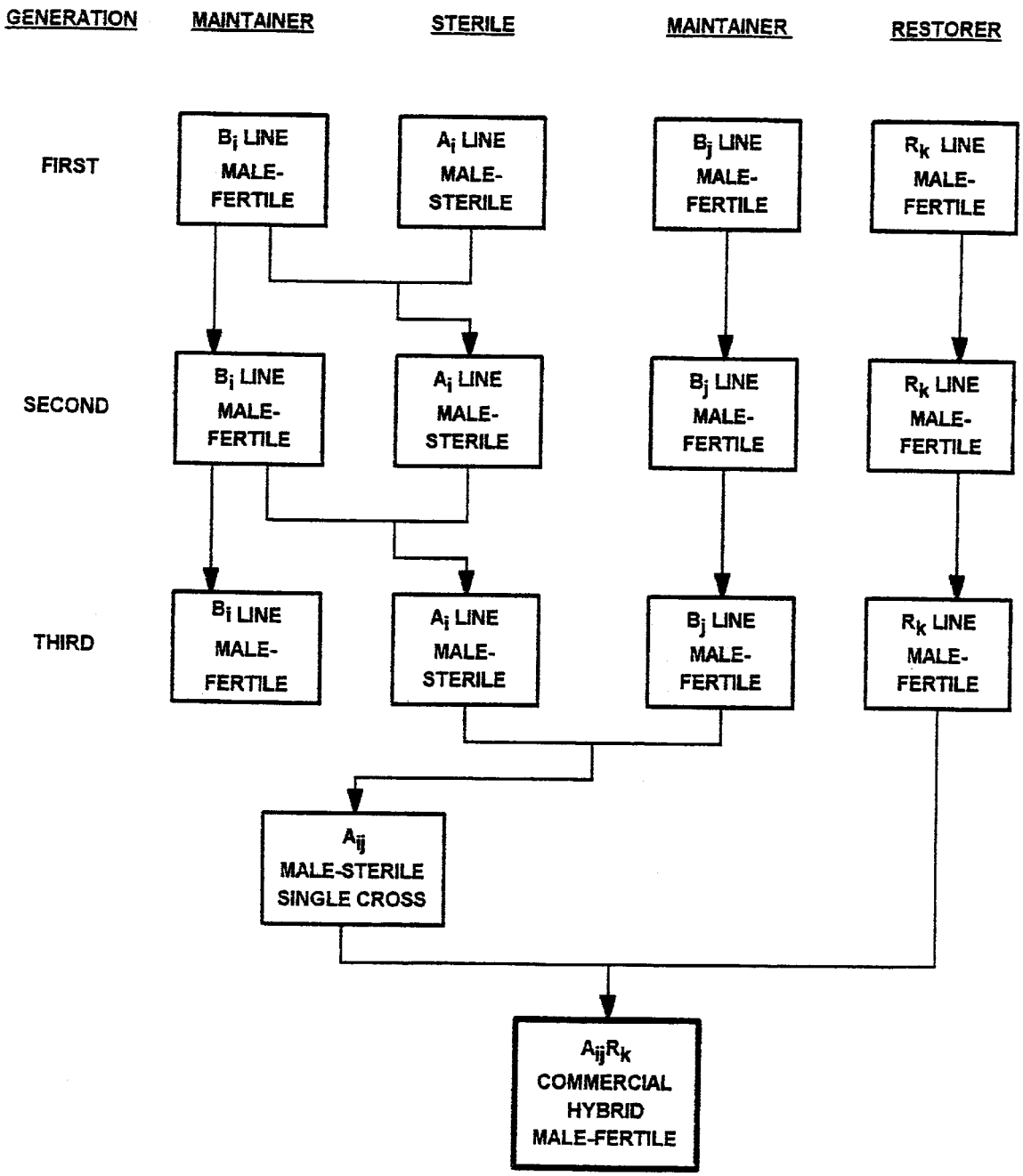
FIG. 3 illustrates a flow diagram showing the production of a three-way cross or modified single cross using the CGMS system.

Modified single cross hybrid—A modified single cross hybrid is designated $A_{ij}/R_k \rightarrow A_{ij}R_K$ and results from crossing a sterile single cross to an R line as shown in FIG. 3. $A_i$ and $B_j$ are related lines so that only modest heterosis would be expressed by $A_iB_j$.

Three-way cross hybrid—A three-way cross hybrid is similar to a modified single cross hybrid except that $A_i$ and $B_j$ are not related. Therefore normally more heterosis is expressed in the $A_{ij}$ cross.

Figure 4:
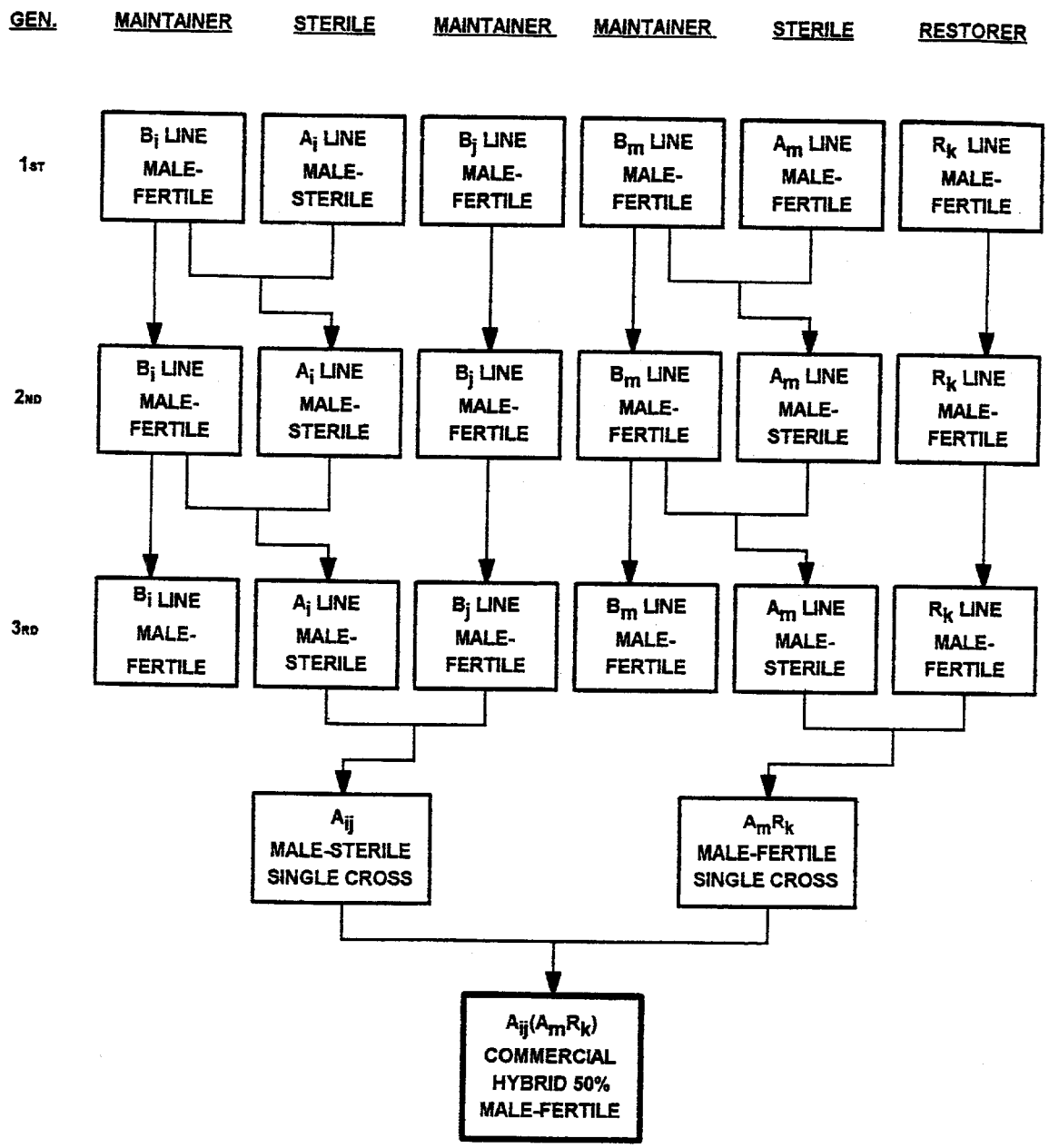
FIG. 4 illustrates a flow diagram showing the production of four-way hybrid cross using the CGMS system.

Double cross hybrid—A double cross hybrid is designated $A_{ij}A_MR_K$ and is produced from crossing two single crosses $A_{ij}$ and $A_MR_K$ as shown in FIG. 4. Performance of both seed and pollen parent are enhanced by using single crosses. This hybrid produced using CGMS is 50% male sterile and moderately variable.

Heterosis—The term heterosis is the superiority of a hybrid in vigor, grain yield, or other characteristics when compared to another genotype. Heterosis can be expressed as a trait difference (e.g. yield) between a given hybrid versus 1) the best competing standard, non-hybrid variety, or alternatively versus 2) one parent of the hybrid which has the highest value for the trait, also known as High Parent Heterosis.

Line—A line is a group or set of related plants reproduced by inbreeding which are phenotypically and genotypically similar and more or less true breeding.

Test cross—A test cross is a cross of a male sterile plant or line ($C_s$msms) to a fertile line of unknown composition. This test cross is made to determine the unknown's genetic factors for nuclear and cytoplasmic male sterility.

Combining ability—The term combining ability refers to the ability or property of a line to produce a level of heterosis in hybrid combinations.

Figure 1:
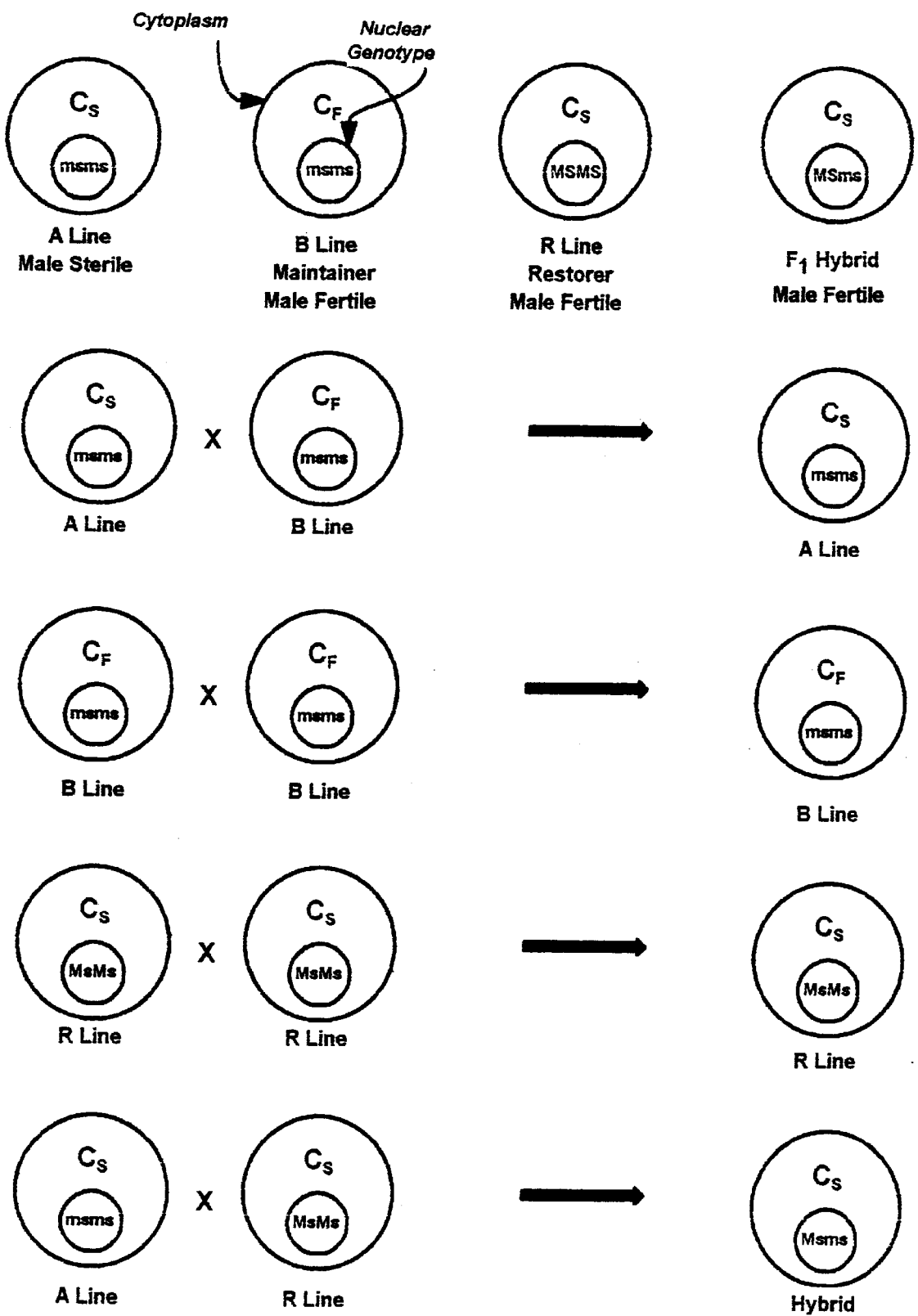
FIG. 1 illustrates an overview of the cytoplasmic-genetic male sterility system (CGMS) to produce $F_1$ hybrids.

Cytoplasmic-Genetic Male Sterility System (CGMS)—The term Cytoplasmic-Genetic Male Sterility System (CGMS) refers to a plant genetic system controlling male fertility and sterility. This system requires a maternally inherited or cytoplasmic component and a nuclear component which follows Mendelian inheritance. Three total components, A, B, and R lines are shown in FIG. 1.

Cytoplasm—The term cytoplasm refers to the maternally inherited DNA component of CGMS system, where $C_s$ is the designation for sterile and $C_F$ is the designation for a fertile DNA factor.

Nuclear male sterile gene—The term nuclear male sterile gene is a Mendelian gene controlling male sterility in conjunction with a cytoplasmic factor. Ms is the designation for the dominant allele for fertility; while ms is the designation for the recessive allele which confers sterility in the homozygous (msms) state and only in presence of the $C_s$ genetic factor.

A Line or $A_i$ Line—An A line ($A_i$) is the male sterile female line "I" used as the seed producing parent in hybrid seed production. "I" indicates a specific line number.

B Line or $B_j$ Line—A B line ($B_j$) is the male fertile maintainer line "j" which is used to assist in propagating the phenotypically identical (but male sterile,) counterpart A line, i.e. $A_i/B_j \rightarrow A_i$. Also used to make sterile single crosses if $A_i$ is a different line from $B_j$.

R Line or $R_K$ Line—The R line ($R_k$) is the male fertile restorer line "$R_k$" used as male parent in hybrid seed production. This R line when crossed with an $A_i$ line restores male fertility to the hybrid seed which is produced from this $A_i/R_k$ cross.

Pollen Flow—The term pollen flow refers to the level of pollen which can be transferred by air movement from a male pollen fertile line to a female male-sterile line in a production field.

The cytoplasmic-genetic male sterility system (CGMS) of the present invention allows the commercial production of hybrid wild rice. All genetic components (A, B, and R lines) of a CGMS system have been developed from proprietary cultivated wild rice populations. It was determined that wild rice populations differ in the frequency of sterile cytoplasm ($C_s$) and in the frequency of a male-sterile (non-restoring) nuclear gene (ms). Unexpectedly, substantial heterosis for grain yield and improved uniformity have been observed in selected hybrids compared to the best current commercial open-pollinated wild rice varieties. Also, the pollen flow and inbred line performance allow efficient production of hybrid wild rice seed for planting purposes.

Male-sterile wild rice plants are distinguishable from fertile plants because of the arrangement and color of male flowers. The term "bottlebrush" has been applied to these plants in Minnesota because of this distinct appearance. In the present invention, the development of male fertile maintainer lines and male fertile restorer lines involved a multi-step approach including test crossing each plant to a male sterile plant or line and evaluating the sterility or fertility of the resulting progenies. Each plant was also self-pollinated to observe its progeny and to preserve a controlled seed line. Most test crosses produced ambiguous or intermediate results. Only a few test crosses gave clear-cut reactions which were the beginning of the new B or R lines of the present invention.

The current use and research involving male steriles in Minnesota wild rice varieties focuses on their value per se in the variety, and not on their use in producing hybrid seed. This research has found that male-sterile plants yield more per plant than fertile plants (Porter, R. A. et al., Wild Rice Breeding, In: Minnesota Wild Rice Research, University Minnesota Agriculture Experiment Station Miscellaneous Publication 64–1990, pp. 24–37, 1989; Porter, R. A. and Schumer, H. J., Wild Rice Breeding. In: Minnesota Wild Rice Research, University Minnesota Agriculture Experiment Station Miscellaneous Publication 74–1992, pp 35–46, 1991). In contrast, the present invention uses the male sterile plants to produce hybrid seed. The male sterile plants of the present invention are not reproducible and male steriles can only be expected to occur in some frequency, roughly, up to a maximum of 50%, in populations. Our method allows the specific, predictable production of male sterile, A line progenies, as shown in Example 13.

The present invention is the first use of inbred wild rice lines to produce hybrid wild rice plants, even for research breeding purposes. Current methods of wild rice breeding utilize highly heterozygous parental plants for crossing in an attempt to create new genotypic combinations. The distinction is that the first generation, $F_1$, or hybrid progeny from crossing two inbred lines are heterozygous, but homogeneous (i.e., uniform), whereas the progeny of crosses between heterozygous plants are both heterozygous and heterogeneous (i.e., variable).

One critical step in a CGMS hybrid system is the development of inbred lines. The inbreeding process in wild rice produces a severe fallout, or loss of lines, due to multiple genetic defects. The attrition rate is extremely high. For example, in one sample of 259 foundation plants subjected to self-pollination, only 28% survived to the $S_3$ generation. Through extensive research, several inbred lines were identified and propagated. In contrast, the wild rice program at University of Minnesota has relied on breeding methods which avoid inbreeding, since the University of Minnesota researchers have previously experienced many problems with inbreeding depression.

Although wild rice is monoecious and partially protogynous, substantial self-pollination normally occurs. There is a one to three day overlap of stigma receptivity and pollen release within individual panicles, which could account for a minor amount of self-pollination. The larger contribution of self-pollinated seeds comes from the extended period over which sequential panicles of wild rice emerge. The receptive female panicle region emerges from the enveloping leaf sheath in the immediate vicinity of the male region of previously emerged panicles. Pollen production is copious, and substantial selfing occurs.

Substantial self-pollination in standard OP varieties of wild rice is easily demonstrated. In initiating inbreeding within populations, the success of single individual OP plants was evaluated. Even prior to initiating forced inbreeding, approximately 20% of seedlings were abnormal, weak, slow growing, or otherwise obviously defective. Many seedlings died at this stage despite having greenhouse care. Furthermore, during extensive germination tests of seed lots performed on standard OP varieties, numerous lethal, semi-lethal abnormalities, and slow-growing types were observed. This genetic load significantly detracts from the performance of the varieties. The abnormalities are similar to those observed once forced inbreeding has commenced. These observed abnormalities are typical of variable populations subjected to inbreeding.

One essential factor for successful hybrid production is heterosis or hybrid advantage over commercial varieties. Prior to our research, no information was available in wild rice regarding potential heterosis. Heterosis in the wild rice hybrids of the present invention was determined to be much higher than expected. Hybrids tested to date have been made by crossing lines from NC-3, NC-5, or a direct progenitor of both. Thus, all lines were derived from similar, related sources. The levels of heterosis observed (30 to 67% higher than open-pollinated controls) as shown in Table 11 is unexpected given the restricted genetic base sampled. In other crops in which hybrids are used, higher levels of heterosis normally come from parental lines having dissimilar and diverse origins. Thus, by using more divergent populations to develop inbred lines for crossing to existing elite inbreds, even higher levels of heterosis in wild rice may be achievable.

Conventionally, heterosis is expressed as hybrid performance relative to performance of the best parent in a hybrid. Trials in wild rice indicate that inbred lines, because of intense inbreeding, are inferior in grain yield, on the average, to OP varieties as shown in Tables 1 and 2. Because of this disparity, the higher yielding OP varieties have been used to determine the level of heterosis in the $F_1$ hybrid.

TABLE 1

Grain yield of hybrids, inbred parental lines, and an OP variety in a replicated yield trial during 1991

| Entry Hybrid | Grain Yield (kg/ha) | Group Mean (kg/ha) |
| --- | --- | --- |
| A4/R4 | 2,824 | 1,617 |
| A1/R4 | 2,032 | |
| A1/R1 | 1,978 | |
| A1/R2 | 1,891 | |
| A4/R3 | 1,785 | |
| A1/R3 | 1,747 | |
| A5/R2 | 1,013 | |
| A1/R7 | 961 | |
| A5/R7 | 319 | |
| Inbred | | |
| R2 | 1,370 | 794 |
| R3 | 866 | |
| R4 | 679 | |
| R1 | 260 | |
| OP Variety | | |
| NC-3 | 1,690 | 1,690 |

TABLE 2

Comparison in yield potential among the entries from yield trial in 1993

| Entry | Grain Yield (kg/ha) |
| --- | --- |
| Hybrid | |
| A1/211-12-3 | 4391 |
| A1/R4 | 4283 |
| A1/R7 | 3407 |
| A1/R2 | 3228 |
| Inbred | |
| B1 | 1896 |
| OP Variety | |
| NC5 | 3417 |
| NC3 | 3039 |

One well documented obstacle to hybrid production in Oryza is lack of pollen production. Pollen flow in the seed production field must be adequate to achieve good seed set on the male-sterile plants. As shown in Table 16, the male-sterile plants of the present invention can be several to 10 meters distant from the pollen source and still have been adequate to make hybrid seed production.

The hybrid wild rice production method of the instant invention requires the crossing together of inbred lines so that one line is pollinated entirely by another line. The lines are so chosen as to produce a known superior performing hybrid. The inbred lines are much more uniform for plant height and maturity than the original base population from which the lines were derived, and uniform hybrids result. The inbreds are easy to maintain because contaminants are readily apparent, and genetic shift does not occur, i.e. lines do not evolve nearly as much as variable populations.

The effective, efficient crossing together of inbred lines is made feasible by male sterility. Plants of one line (the seed parent) produce no pollen and, therefore, must be pollinated by another line (the pollinator). Mere mixing of male fertile inbred lines to promote hybridization cannot be effective because substantial amounts of self-pollination occur. Using the male sterile approach, planting seed is harvested only from the sterile plants; the pollinator plants are normally discarded. The use of male sterility replaces enormous quantities of hand labor. The importance of CGMS is that is provides for the production of seed parents which are 100% male sterile.

To produce a 100% sterile line requires an A line plant possessing both the nuclear and cytoplasmic factors for male sterility, msms and $C_S$, respectively, as shown in FIG. 1. When this A line plant is pollinated by a maintainer, or B line, only sterile progeny result. The B line also possesses msms, but is male-fertile because of its cytoplasmic factor $C_F$. The B line may be phenotypically indistinguishable from the A line or have varying degrees of differentiation. The A line is subsequently crossed with a restorer (R) line. The R line is male fertile, but is distinct from the B line. The R line may have either fertile or sterile cytoplasm (preferably sterile), but has nuclear genotype MsMs which causes all progeny to be fertile. B lines and R lines can propagate themselves.

The CGMS system of the present invention can be used several different ways to produce hybrids. In one preferred embodiment, the A and B are phenotypically identical and when crossed, result in a single cross $F_1$ hybrid as shown in FIG. 2. In another preferred embodiment, a second B line is introduced, as shown in FIG. 3, then a modified single cross or a three-way cross results. Which depends on the relatedness of the A and B lines. If the A and B are closely related, the cross actually resembles a single cross (hence "modified" single cross); if the A and B are unrelated a three-way cross results. The key intermediate step is the production of a sterile single cross, denoted $A_{ij}$ in FIG. 3, which is subsequently crossed to an R line.

In another preferred embodiment, the sterile single cross can be crossed to a pollinator which is itself a hybrid (fertile single cross) to produce the double or four-way cross as shown in FIG. 4.

EXAMPLES

The following examples are provided to further illustrate the present invention and are not intended to limit the invention beyond the limitations set forth in the appended claims.

Example 1
Overview of the Method of Developing A, B, and R lines

The first step in developing a new line to use in the CGMS system of the present invention was to cross a desired unknown plant or inbred line, as male, to a uniform male sterile A line, such as A1. This was the "test cross." Simultaneously, the pollinator line was self-pollinated. This generated the "selfed progeny." The test cross and selfed progeny were evaluated for sterility at flowering time. The unknown was classified into one group i.e., potential B line or R line use as shown in Table 3.

B Line Development

If the unknown was identified for potential B line use, then the unknown plant was continually self-pollinated, test crossed, and selected for several generations to achieve uniformity of the following two types:

1. The test cross was uniformly male sterile. By selecting selfed progeny whose companion test cross was uniformly male sterile, the selfed progeny was free from genes conferring pollen fertility restoration. The B line must be capable of producing more than 98% male sterile plants when crossed to A lines. This step required from three to as many as six to eight generations to achieve.

2. The selfed progeny was phenotypically uniform. This is not an absolute, as heterozygosity decreases by one-half with each generation of self pollination, but normally five generations is sufficient, being the level at which more than 95% of heterozygosity has been eliminated.

Relationship between B Lines and A Lines

The A line development is secondary to B line development and is most economically done simultaneously with a companion B line. A lines were developed to genotypically and phenotypically mimic their associated B lines. A lines have no independent identity, only that of the companion B line. Thus, an individual male-sterile plant identified within an OP population cannot be preserved or propagated. In contrast, male fertile B line plants which can be self-pollinated rapidly assume a distinct, independent identity.

Therefore, while male sterile plants have been previously identified, they do not comprise A lines as described in the present invention. The A lines claimed herein can only be developed once a target B line is identified or developed. However, once developed, A lines are propagable indefinitely by following the procedure diagrammed in FIG. 1.

A further distinction exists between A lines and the random male steriles observed in OP populations. Progeny from male sterile plants in OP populations may include male sterile plants in frequencies ranging from 9% to roughly 50%. However, it is impossible to predict which individuals will be male sterile, or even the percentage of male sterile plants in such a progeny. There is no control or predictability.

In contrast, when an A line is pollinated with a B line, as in Example 14, it can be said with a high degree of certainty that essentially all the progeny will be male sterile, i.e. predictability and control have been established. Predictability and control are important for the practical utilization of the male sterility gene.

A Line Development

Many of the steps of A line development are the same steps used in development of the companion B line. They are repeated here to provide the perspective from A line side. A target B line or plant was selected and crossed to a male sterile line, e.g. A1. The male sterile progeny of this test cross are crossed to the fertile B line parent. Note that it was the progeny which were subsequently crossed, not the original sterile line. This process was repeated throughout the period of B line development. The tester most frequently used to monitor the progress of B line development is the developing associated A line itself. This procedure of continually crossing the test cross progeny to the B line steadily converted the original nuclear genotype of the original A line into that of the donor B line. Not only did the original A line genes become replaced by new B line genes, but the A line became inbred as the B line did. The A line was always at least one generation less inbred than the companion B line, because the original selfed B line progeny was grown with its non-bred test cross.

In early generations, A lines were quite distinct from their B line counterparts, due both to incomplete gene substitution and less inbreeding. However, after approximately 5 generations of crossing, the A lines are more than 95% B line genotype and more than 90% of original heterozygosity had been eliminated.

R Line Development

An identified R line candidate was developed by procedures similar to B line development, except that selection during inbreeding was based on a high degree of fertility (absence of sterility) in test crosses. No A line counterpart was developed concomitantly with an R line. Criteria of acceptable uniformity in R line development is the same as that for B lines. This generally requires 5 or more generations of self-pollination to achieve more than 95% homozygosity.

Example 2

The development of the CGMS System in Wild Rice

The wild rice CGMS system of the present invention has been developed from within individual proprietary populations NC-1, NC-3 and NC-5. The performance of the existing source populations was not affected by the presence of these CGMS system components. NC-3 and NC-5 were derived from NC-1.

A low frequency (1–3%) of male-sterile plants had been observed in wild rice populations grown in California. Sterility is readily determined in the field. Staminate floral branches on such plants normally remain appressed and individual florets either do not open at all or open abnormally. In sterile plants anthers are either absent or shriveled with a dark tan color. Anthers on fertile plants are plump and bright yellow.

To observe the male steriles, several populations were grown in maternal half-sib family groups. The resultant individual families varied in the frequency of male sterile plants. Unexpectedly, occasional families possessed 20–40% sterile plants. Since wild rice is assumed to be highly out crossed, being monoecious and protogynous, the high sterile plant frequencies could not be explained based on models allowing segregation of only genetic male sterility under random mating. However, it was determined that cytoplasmic factors for sterility were also present, which explained the high frequencies of male-sterile plants in a family.

Test crosses of male-sterile plants to males from unrelated half-sib families were made in 1990. In 1991, both the testcross progenies and self-pollinated progenies of the male plants were scored for amount of sterility. Testcross and selfed progenies were either uniformly sterile, segregating for fertility, or were uniformly male-fertile.

The genotypic and phenotypic arrays expected in a population polymorphic for both cytoplasmic and nuclear sterility factors were constructed to serve as a model as shown in Table 3. Assumptions for this model included a sporophytic, single dominant restorer and a single cytoplasm-conditioned sterility factor system.

TABLE 3

Expected progeny test results for male fertility in a population polymorphic for both cytoplasmic and nuclear sterility factors

| Male Sterile | Progeny Test | | |
|---|---|---|---|
| $C_S$msms/Unknown[a] | Test Cross | Male Selfed | Use |
| $C_S$Msms | Seg 1:1 | Seg 3:1 | R line[b] |
| $C_S$MsMs or $C_F$MSMS | Fertile | Fertile | R line[c] |
| $C_F$msms | Sterile | Fertile | B line |
| $C_F$Msms | Seg 1:1 | Fertile | B line[d] |

[a]Known from results of progeny tests.
[b]Requires additional inbreeding and selection to eliminate ms.
[c]Requires additional test crossing to separate ambiguous $C_F$ type from $C_S$.
[d]Requires additional inbreeding, test crossing and selection to eliminate Ms.

As shown in Table 4, the frequency (F) of male sterile plants ($C_s$msms) in these two populations ranged from 2.0% in NC-5 to 3.6% in NC-3. While the difference in $F(C_s$msms$)$ was not large, it was determined that variation between populations in $F(C_F)$ confounded the comparison by preventing expression of sterility in a significant portion of msms plants (those which are ($C_F$msms).

Because testcross females (testers) are $C_s$msms, testcross progenies were used to provide classical genetic testcross information on the male parents. $F(C_s$msms$)$ plants ranged from 0.264 (NC-5) to 0.481 for NC-3 in topcross data combined over families as shown in Table 4. These values directly represent estimates of F(ms) in the base populations. Thus, with the effect of $C_F$ removed, large differences in F(ms) were detected, and F(ms) was much higher than expected from previous open pollinated (OP) population data.

TABLE 4

Frequency of male-sterile ($C_S$msms) individuals in OP base populations and within topcrosses of fertile individuals onto male sterile testers

| Base population | 0.036 | 0.020 |
|---|---|---|
| No. individuals | 87 | 400 |
| Reference Population | NC-3 | NC-5 |
| Test crosses | | |
| $C_S$msms/Male | 0.481 | 0.264 |
| Number testcross males | 44 | 24 |
| Total number individuals | 695 | 344 |

A second estimate of F(ms) was obtained by classifying testcross families into three types based on their segregation reaction. The three classes correspond to specific genotypes in the parent population. Thus, uniformly fertile, segregating (1:1), and uniformly sterile top cross progenies represent C__MsMs, C__Msms and $C_F$msms parental genotypes, respectively. As shown in Table 5, the two estimates of F(ms) (which are correlated because they are estimated from the same sample of families), agreed quite well for NC-3 and NC-5. Subsequent analyses which required the use of F(ms) utilized the mean value.

TABLE 5

Frequency of allele for genetic male sterility (ms) in two populations

| Progeny Type | NC-3 | NC-5 |
|---|---|---|
| Combined testcross segregation | | |
| Number of Individuals | 695 | 344 |
| F(ms) | 0.481 | 0.264 |
| Testcross family classification | | |
| Number families segregating | 21/44 | 7/24 |
| F(ms) | 0.477 | 0.271 |
| Mean F(ms) | 0.479 | 0.268 |

As shown in Table 6, joint consideration of top crossed/selfed progeny pairs separated testcross parents into four classes. Two classes, $C_S$MsMs and $C_F$MsMs, are indistinguishable without reciprocal test crosses involving a maintainer line ($C_F$msms) as male, and are combined in the summary. Frequency of the sixth class ($C_S$msms) was estimated directly from the OP observations reported above (see Table 4). Progeny pair classification permits the calculation of $F(C_F)$ by comparing frequencies of classes 4 and 5 versus classes 1 and 2 (Table 6). NC-3 was nearly fixed for fertile cytoplasm, $F(C_F)=0.912$, while NC-5 had $F(C_F)=0.620$.

TABLE 6

Observed frequencies of five CGMS genotypes in two populations of wild rice and an estimate of $F(C_F)$. Classification was based on test crossed/selfed family pairs

| Genotype | NC-3 | NC-5 |
|---|---|---|
| $C_S$msms[a] | 0.036 | 0.020 |
| $C_S$Msms | 0.029 | 0.089 |
| $C_S$MsMs + $C_F$MsMs | 0.263 | 0.712 |
| $C_F$msms | 0.234 | 0.000 |
| $C_F$Msms | 0.438 | 0.175 |
| Total | 1.000 | 1.000 |
| Number family pairs | 33 | 11 |
| Frequency of $C_F$[b] | 0.912 | 0.620 |

[a]Estimated directly from OP population data.
[b](F($C_F$msms) + F($C_F$Msms))/(F(C__msms) + F(C__Msms)).

Independent estimates of F(ms) and $F(C_F)$ allow joint calculation of nuclear genetic and cytoplasmic expectations for NC-3 and NC-5 and comparisons of expectation to observation. Such calculation of expectations requires independence of nuclear and cytoplasmic components. As shown in Table 7, both NC-3 and NC-5 were found to satisfactorily fit the model using a Chi square ($X^2$) test. Degrees of freedom (df) were subtracted in both analyses for: 1) forcing total deviations to zero, 2) estimating F(ms), and 3) estimating $F(C_F)$. An additional df was subtracted in the NC-5 analysis because the two smallest classes were pooled.

TABLE 7

Observed and expected frequencies of the six combinations of cytoplasm and nuclear genotype in two wild rice populations

| | NC-3 Frequency | | NC-5 Frequency[a] | |
|---|---|---|---|---|
| Genotype | Observed | Expected | Observed | Expected |
| $C_S$msms | 0.036 | 0.020 | 0.020 | 0.027 |
| $C_S$Msms | 0.029 | 0.044 | 0.089 | 0.149 |
| $C_S$MsMs + $C_F$MsMs | 0.263 | 0.271 | 0.712 | 0.536 |
| $C_F$msms | 0.234 | 0.209 | 0 | 0.044 |

TABLE 7-continued

Observed and expected frequencies of the six combinations of cytoplasm and nuclear genotype in two wild rice populations

| | NC-3 Frequency | | NC-5 Frequency[a] | |
|---|---|---|---|---|
| Genotype | Observed | Expected | Observed | Expected |
| $C_F$Msms | 0.438 | 0.455 | 0.178 | 0.243 |
| Total | 1.000 | 1.000 | 1.000 | 1.000 |
| $X^2$ | 0.021 | | 0.142 | |
| df | 2 | | 1 | |
| | P > 0.95 | | 0.50 < P < 0.75 | |

[a]$C_S$msms and $C_F$msms were combined due to small individual expeptations. Four classes remained which resulted in additional reduction of 1 df.

Example 3

A summary of the above data is shown in Table 8 which indicates that NC-3 and NC-5 are different in population composition. Hence, the populations differed in suitability for isolation of hybrid parent lines. NC-3 had approximately 67% plants which will either directly produce maintainers or will produce maintainers following additional generations of progeny testing to eliminate heterozygous maintainers/restorers ($C_F$Msms). Restorers and restorer sources are present at less than 7% in NC-3. Additionally, $C_S$MsMs types cannot be distinguished from $C_F$MsMs types without a reciprocal testcross using a $C_F$msms male and selfing of subsequent $F_1$'s. $F_2$ progeny of $C_S$MsMs female involved in such a cross will segregate 3:1 while the analogous cross made with $C_F$MsMs females will not. More than 90% of MsMs genotypes in NC-3 are expected to possess $C_F$.

In contrast, NC-5 represented a source of fewer maintainers (4.4%) than NC-3 (20.9%) and a source of fewer potential maintainers from the segregating individuals (24.3% versus 45.5%). However, NC-5 had a far richer source of restorers (20.4%) and potential restorers (14.9%) than NC-3, 2.4% restorers and 4.4% potential restorers.

TABLE 8

Potential B and R lines identified by Test crosses arising from two populations of wild rice; excluding $C_F$MsMs lines (1991 sampling)

| Original Plant | NC-3 | NC-5 | Potential Use |
|---|---|---|---|
| $C_S$MsMs | 3 | 15 | R line |
| $C_S$Msms[a] | 12 | 27 | R line |
| $C_F$msms | 25 | 2 | B line |
| $C_F$Msms[b] | 39 | 30 | B line |
| n | 93 | 92 | |

[a]Requires additional generation(s) of selfing, test crossing, and evaluating to recover $C_S$MSMS type.
[b]Requires additional generation(s) of selfing test crossing, and evaluating to recover $C_F$msms type.

The ultimate importance of isolating both restorers and maintainers from single populations (i.e., generalized sourcing) versus isolating each type from separate population (i.e., specialized sourcing) is not known at this time.

Example 4

Additional Inheritance Information of the Genetic Male Sterile Factor

Additional information on the inheritance of the genetic male sterility factor was obtained by examining testcross segregation ratios. Twenty-three testcross families were examined in each of two populations of male sterile x heterozygous male fertile plants. In a single gene model, the expected segregation was 1:1. As shown in Table 9, the overall goodness of fit was excellent by a $X^2$ test. This data supported the hypothesis of single gene control of male sterility in the presence of sterile cytoplasm $C_S$.

TABLE 9

Frequency of male sterile plants within testcross families segregating for male sterility. $X^2$ test is for goodness of fit to a 1:1 ratio

| Source Population | No. Families | Number Plants Fertile | Sterile | $X^2$ | df | P |
|---|---|---|---|---|---|---|
| NC-5 | 23 | 113 | 104 | 0.37 | 1 | >0.99 |
| NC-3 | 23 | 91 | 111 | 1.98 | 1 | >0.99 |
| Pooled | 46 | 204 | 215 | 0.29 | 1 | >0.99 |

Example 5
Stability of Inbred Line Performance

The data shown in Table 9 regarding the frequency and occurrence of the various genotypes and cytoplasms addressed a single generation of information. A, B, and R lines are only useful if their characteristic phenotype is maintained over several generations. As shown in Table 10, stable A/B pairs and R line have been developed which can be used to produce the wild rice hybrids of the present invention.

In some cases, the earliest generation reported may not be uniform for fertility or sterility because of residual segregation of the B or R line. Additional generations of selfing, test crossing, evaluation, and selection have been effective in many such cases. The infrequent fertile which are in the later generation A lines, e.g. $A_1/B_1$ (=$A_1$), are believed due to pollen contamination.

Calif. in each year, and also at a second location (Gridley, Calif.) in 1994. The entry list changed from year to year as information accumulated to discard inferior inbred lines and hybrids. For each trial, only data for high-performing hybrids are shown in Table 11. In all trials, the "Entries" mean square was highly significant. Numerous wild rice hybrids yielded 30–67% higher than the controls, which were NC-3 and NC-5.

TABLE 11

Yield of selected hybrids versus OP controls over three years

| | | Yield[a] | | | | | |
|---|---|---|---|---|---|---|---|
| | | 1991 | | 1993 | | 1994[b] | |
| Entry | Type | kg/ha | % | kg/ha | % | kg/ha | % |
| A4/R4 | Hybrid | 2820 | 167 | | | | |
| A1/R4 | Hybrid | | | 3500 | 133 | 3660 | 134 |
| A1/R211-12-3 | Hybrid | | | 3590 | 136 | | |
| A1/RNC5-37-2 | Hybrid | | | | | 4280 | 154 |
| ANC3-54-1/R4 | Hybrid | | | | | 4540 | 163 |
| A409-1-3/R4 | Hybrid | | | | | 4250 | 153 |
| A211-12-3/R4 | Hybrid | | | | | 4270 | 153 |
| NC-5 | OP | | | 2790 | 100 | 2580 | 100 |
| NC-3 | OP | 1690 | 100 | 2480 | | 2980 | |
| LSD$_{0.05}$ | | 560 | | 480 | | 650 | |
| df | | 12 | | 12 | | 56 | |

[a]Yield (%) relative to mean performance of NC-3 and NC-5 controls.
[b]Two locations in 1994.

The mean grain yield of a random group of hybrids equaled the control yield in 1991 and 1993. However, variation in yield among hybrids was very large. The 1994 trials consisted of a more select group of hybrids, because A1 and R4, at least one of which appeared in every hybrid, had been found to have good combining ability from the

TABLE 10

Isolation of B and R lines with reproducible ability to maintain sterile lines (B Lines) or to restore fertility (R Lines)

| Pair Designation | Type | 1993 Field | | | 1993–94 Greenhouse | | | 1994 Field | | |
|---|---|---|---|---|---|---|---|---|---|---|
| | | Level | Fertile | Sterile | Level | Fertile | Sterile | Level | Fertile | Sterile |
| B Lines | | | | | | | | | | |
| 409-1-1 | B | $S_4$ | 20 | 0 | $S_5$ | 8 | 0 | $S_6$ | 10 | 0 |
| A1/409-1-1 | A | $F_1$ | 0 | 20 | $BC_1$ | 0 | 3 | $BC_2$ | 0 | 9 |
| NC3-54-1 | B | $S_1$ | 5 | 0 | $S_2$ | 12 | 0 | $S_3$ | 21 | 0 |
| A1/NC3-54-1 | A | $F_1$ | 0 | 5 | $BC_1$ | 3 | 1 | $BC_2$ | 0 | 30 |
| NC5-16 | B | $S_1$ | 17 | 0 | No Data | | | $S_2$ | 43 | 0 |
| A1/NC5-16 | A | $F_1$ | 2 | 9 | No Data | | | $BC_1$ | 0 | 41 |
| B1 | B | $S_5$ | 52 | 0 | $S_6$ | 29 | 0 | | | |
| A1/B1 | A | $BC_2$ | 6 | 124 | $BC_3$ | 6 | 67 | $BC_4$ | 3 | 57 |
| R LINES | | | | | | | | | | |
| NC5-78 | R | $S_1$ | 5 | 3 | No data | | | $S_2$ | 15 | 0 |
| A1/NC5-78 | A/R | $F_1$ | 4 | 17 | No data | | | No data | | |
| 505-6-1 | R | $S_4$ | 20 | 0 | $S_5$ | 21 | 0 | | | |
| A1/505-6-1 | A/R | $F_1$ | 20 | 0 | | | | $F_1$ | 14 | 0 |
| 505-7-1 | R | $S_4$ | 20 | 0 | $S_5$ | 21 | 0 | | | |
| A1/505-7-1 | A/R | $F_1$ | 20 | 0 | | | | $F_1$ | 11 | 0 |
| 504-9-1 | R | $S_4$ | 20 | 0 | $S_5$ | 9 | 0 | | | |
| A1/504-9-1 | A/R | $F_1$ | 20 | 0 | | | | $F_1$ | 15 | 0 |

Example 6
Hybrid Wild Rice Performance and Evaluation of Heterosis

Replicated experimental yield trials which compared single cross hybrids ($A_i/R_k$) with OP varieties were conducted in 1991, 1993 and 1994. Trials were at Woodland, previous tests. No wild rice hybrid (n=13) yielded less than the OP controls in 1994.

Vegetative stage hybrid vigor was evident as well. As shown in Table 12, tiller development in hybrids was more rapid than with the controls.

TABLE 12

Time course of tiller number per plant for hybrids versus OP controls in 1993.

| | | Tiller number at days after July 1 | | | | |
|---|---|---|---|---|---|---|
| Entry Group | N | 28 | 35 | 42 | 49 | 56[a] |
| Hybrids | 2 | 6.6 | 7.2 | 7.4 | 7.4 | 7.2 |
| OP Controls | 2 | 4.8 | 5.7 | 6.4 | 6.8 | 6.4 |

[a]Represents final panicle number per plant at maturity

Example 7
Uniformity

Variation in plant height and maturity within OP populations has made wild rice production difficult to manage. Consequently, individual plants were scored for these traits in the yield trials in 1991 and 1993 for height only. Within-plot variances were pooled over replications for comparison by $X^2$ homogeneity tests. Hybrids and inbred lines, as groups, were much less variable than NC-3 for plant height in 1991 and 1993 and for flowering date in 1993, as shown in Table 13.

TABLE 13

Individual plant standard deviations (S) for plant height and days to flower for hybrids, inbreds, and OP populations. Plant height was analyzed in 1991 and 1993, while flowering date was analyzed only in 1991

| | Plant Height | | | | Days to Flower | |
|---|---|---|---|---|---|---|
| | 1991 | | 1993 | | 1991 | |
| Entry Group | N | S cm | N | S cm | N | S days |
| Hybrids | 9 | 14.0 | 4 | 11.7 | 9 | 1.6 |
| Inbreds | 4 | 12.2 | 1 | 14.4 | 4 | 1.8 |
| OP Control | 1 | 20.6 | 2 | 20.2 | 1 | 3.0 |

The data depict variation among individuals within hybrids, inbreds, and varieties. The contrast between the hybrids and OP varieties in both flowering date and height variation are also readily apparent visually in the field. This marked reduction in variation in wild rice hybrid will result in improved management and quality, and increased harvestable yield.

Example 8
Application to Commercial Production

The purpose of developing A, B, and R lines with the CGMS system of the present invention is to produce high-performing $F_1$ hybrid wild rice varieties. There are three methods of use.

The simplest method of deployment is the single-cross $F_1$ as shown in FIG. 2. In the single-cross, line $A_i$ is perpetually maintained by line $B_i$, where $A_i$ and $B_i$ represent the two phenotypically identical alterative forms of the inbred line "i". This inbred male sterile is then crossed to male line $R_K$ to produce the commercial product. This scheme can be successful if the inbred line i has acceptable vigor and yield.

If Line $A_i$ lacks vigor, it can be crossed with maintainer line $B_j$ prior to final cross to $R_K$. This technique produces the modified single cross or three-way cross as shown in FIG. 3 depending on the relatedness of $A_i$ and $B_j$. If these lines are closely related, the $A_{ij}$ sterile single cross will resemble $A_i$ with little vigor expressed, but the resulting $A_{ij}R_K$ $F_1$ will be quite uniform. The more distant the relationship between $A_{ij}$ and $B_j$, the more potential heterosis which can be produced in the sterile single cross, assuming an appropriate choice of parents. Conversely, more variability will be expressed in the $F_1$, and probably less heterosis than could be achieved with a single cross.

The extreme case, a double cross hybrid, can be used if the $R_K$ inbred male, as well as the female, is too weak for easy commercial production as shown in FIG. 4. This scheme produces the most variable $F_1$ hybrid, with less heterosis expressed, but the most economically produced $F_1$ seed.

Example 9
Heterosis Levels

Higher levels of heterosis were found within the existing group of inbred lines. The initial elite hybrid was A1/R4, which has averaged 33% superiority over OP controls for two years. In 1994, several new A lines were crossed to R4, and several new R lines were crossed to A1. The new A and R lines were not crossed to each other, however, due to the large number of possible combinations. One R line and four B lines produced hybrids exceeding the yield of A1/R4 by 4 to 24% as shown in Table 14. These superior lines have now been crossed inter se.

Also, A1/RNC5-37-2 yields 117% of A1/R4, and ANC3-54-1/R4 yields 124% of A1/R4. The cross ANC3-54-1/RNC5-37-2 has been made and tested in 1995. To the extent that general combining ability is responsible for the superior performance of the hybrids made form ANC3-54-1 and RNC5-37-2, the yield gains should be additive.

TABLE 14

1994 yield performance of hybrids grouped by common female (A1) and common male (R4) parents. Heterotic hybrid A1/R4 = 100%

| Entry A1/_ | Yield relative to A1/R4 | Entry _/R4 | Yield relative to A1/R4 |
|---|---|---|---|
| | | ANC3-54-1 | 124% |
| RNC5-37-2 | 117% | A211-12-3 | 117% |
| | | A409-1-3 | 116% |
| | | A211-10-5 | 104% |
| R4 | 100% | A1 | 100% |

Example 10
Multiple Heterotic Groups

It was unexpected to find two heterotic groups within an individual population or closely related populations. When crossed to form A1/R4, line A1 and line R4 demonstrated 33% heterosis in grain yield above OP controls. Both lines were developed from NC-1, a proprietary Nor-Cal population, source of both NC-3 and NC-5. A third line 211-12-3 was also developed from this population. Because its initial genotype was $C_F$Msms when the line was used for test crossing in the fourth inbreeding generation, both B and R lines, B211-12-3 ($C_F$msms) and R211-12-3 ($C_F$MsMs), respectively, were developed. An A version, A211-12-3 ($C_s$msms), was also created from B211-12-3.

The hybrid A211-12-3/R4 yielded 136% of control while A1/R211-12-3 yielded 153% of control in 1993 yield trial. Table 15 summarizes the performance of all possible hybrids among these three lines.

TABLE 15

Yield performance, relative to OP controls, of all possible hybrids made by crossing three lines derived from a single population

| Hybrid | 1993 Yield % of Control |
| --- | --- |
| A1/R4 | 132% |
| A1/R211-12-3 | 138% |
| A211-12-3/R4 | 153% |

This demonstrates the existence of at least three heterotic groups within a single wild rice population.

Example 11
Recombinant Second Cycle Lines

Inbred lines were all isolated directly from open-pollinated populations.

Numerous excellent A, B, and R lines have been developed. Inbred line performance has been improved by intercrossing B or R lines inter se and isolating new recombinant B or R lines, respectively.

For example, B1 was crossed to BNC3-54-1. Selections from $F_2$ are advanced by self-pollinating, selecting and test crossing. New superior B lines were produced.

Example 12
Backcross-Derived Second Cycle Lines

Existing A, B, and R inbred lines are improved by introduction of single-gene traits; lines or populations with desirable traits (donor) are incorporated into hybrid development program. The donor is used as pollinator to cross to A, B, and/or R lines as recurrent parents. Resulting progenies are crossed as pollinators to original recurrent parents. Process is repeated, with selection for desired trait from donor, until original line is recovered except for the novel trait.

Example 13
Male-sterile Variety

A male-sterile A line is pollinated by a maintainer B line chosen to produce a high degree of heterosis. This cross expresses more heterosis than desired for a sterile single cross used in three-way or four-way crosses. This variety is essentially free of pollen-bearing plants. It has been shown previously that male sterile plants yield more than equivalent male fertile plants. A small percentage of fertile plants is then blended in with the planting seed to provide pollen.

For example, A1/B211-12-3 (Cross 1) is a heterotic single cross essentially free of fertile plants. A1/R211-12-3 (Cross 2) is a phenotypically similar fertile hybrid. A planting seed is created by mixing 90% or more of Cross 1 with 10% or less of Cross 2.

Example 14
Variety Essentially Free From Self-pollinated Seed

Seed lots of open-pollinatedwild ricevarieties contain an undesirable level of seeds which are produced as a result of self-pollination. The hybrid and method of the present invention results in very low to zero levels of self pollinated seed. The A line is essentially devoid of plants producing pollen. Essentially all seeds are produced on A line plants pollinated by an unrelated R line.

Example 15
Pollen Flow

The use of the CGMS system of the present invention to produce hybrid is successful only if pollen is transferred from male-fertile lines (B or R lines) to male-sterile lines (A lines). A lines and B or R lines were grown in adjacent strips 11 m wide in 1994. Seed set percentage on male-sterile plants was excellent at distances up to the limit of the experiment, 10.7 m as shown in Table 16.

TABLE 16

Seed set percentage on male-sterile plants grown at varying distances from a uniform pollen source in 1994

| Distance m | Seed Set % | Standard Deviation % |
| --- | --- | --- |
| 2.1 | 80.9 | 12.2 |
| 4.3 | 84.2 | 5.8 |
| 6.4 | 75.6 | 3.4 |
| 8.5 | 74.0 | 5.7 |
| 10.7 | 80.4 | 7.8 |

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

STATEMENT OF DEPOSIT

A deposit of the NorCal Wild Rice varieties *Zizania palustris* L. (Dore) 'AI', 'RNC5-37-2', 'R4', 'ANC3-54-1' and 'BNC3-54-I' disclosed above and recited appended claims has been made with the American Type Culture Collection (ATCC), 10801 University Blvd., Manassas, Va. 20110-2209. The date of deposit was Dec. 19, 1997 for varieties 'AI' and 'RNC5-37-2' and Jan. 27, 1999 for the remaining variety lines. The deposit of 2,500 seeds were taken from the same deposit maintained by Norcal Wild Rice since prior to the filing date of this applications. All restriction upon the deposit have been removed, and the deposit is intended to meet all of the requirements of 37 C.F.R §1.801–1.809, The ATCC accession numbers are ATCC 209404 for 'AI', ATCC 209405 for 'RNC5-37-2', ATCC 203611, for the variety entited 'R4', ATCC 203612, for the varity entitled 'ANC3-54-1' and ATCC 203613 for the variety entitled 'BNC3-54'. The deposits will be maintained in the depository for a period of 30 years, or 5 years after the last request, or for the effective life of the patent, whichever is longer, and will be replaced as necessary during that period.

What is claimed is:

1. A method of producing $F_1$ hybrid Zizania seed comprising crossing an inbred A line male sterile Zizania plant with an inbred R line Zizania plant and culturing said male sterile Zizania plant until seed is produced therefrom.

2. The method of claim 1, wherein said A line male sterile Zizania plant consists essentially of one member of the group A1 having ATCC Accession No. 209404, ANC3-54-1, having ATCC Accession No. 203612.

3. The method of claim 1, wherein said R line consists essentially of one member of the group R4 having ATCC Accession No. 203611, RNC5-37-2 having ATCC Accession No. 209405.

4. The method of producing $F_1$ hybrid Zizania seed comprising crossing an inbred A line with an inbred B line consisting essentially of BNC3-54-1 having ATCC Accession No. 203613 and culturing a plant of said inbred A line until seed is produced therefrom.

5. A method of maintaining an inbred male sterile Zizania A line by crossing said A line with an inbred B line Zizania and culturing a plant of said male sterile Zizania A line until seed is produced therefrom.

6. The method of claim 1, wherein said Zizania seed produced comprises less than 1.0% self-pollinated seed.

7. A Zizania variety having a percentage of male sterile plants of greater than 75%.

8. The variety of claim 7, wherein said percentage of male sterile plants is between about 75% and about 85%.

9. The variety of claim 7, wherein said percentage of male sterile plants is between about 85% and about 95%.

10. The method of producing seed by growing sterile single cross Zizania plants interspaced in a field with male fertile pollinator plants and culturing said sterile single cross Zizania plants until seed is produced therefrom.

11. The method of claim 10, wherein said male fertile pollinator plants comprise less than 25% of the plants grown in the field.

* * * * *